United States Patent
Allen et al.

(12)

(10) Patent No.: US 6,316,698 B1
(45) Date of Patent: Nov. 13, 2001

(54) PLANT ALPHA-GLUCOSIDASE II HOMOLOGS

(75) Inventors: Stephen M. Allen; Anthony J. Kinney, both of Wilmington, DE (US)

(73) Assignee: E. I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/437,054

(22) Filed: Nov. 9, 1999

Related U.S. Application Data

(60) Provisional application No. 60/107,909, filed on Nov. 10, 1998.

(51) Int. Cl.[7] .............................. A01H 5/00; C12N 5/14; C12N 15/85; C07H 21/04
(52) U.S. Cl. ........................ 800/295; 435/6; 435/91.1; 435/91.3; 435/325; 435/375; 435/419; 536/23.1; 536/23.4; 536/23.6
(58) Field of Search .......................... 435/6, 91.1, 91.3, 435/325, 375, 419; 536/23.1, 23.4, 24.5, 24.3, 24.33, 24.37; 800/295; 534/23.6

(56) References Cited

U.S. PATENT DOCUMENTS 5,763,252   6/1998   Skadsen et al. ............... 435/200

OTHER PUBLICATIONS

Sugimoto et al., (1997) Plant Mol. Biol. 33:765–768.

Kalz–Fuller et al., (1995) Eur. J. Biochem 231:344–351.

Trombetta et al., (1996) J. Biol. Chem., 271:27509–27516.

Taylor et al., (1998) Plant J. 13:419–425 "PMID:9680991, UI:98345969".

Tibbot and Skadsen (1996) Plant Mol. Biol. 30:229–241.

NCBI General Identification No. 2648032.

NCBI General Identification No. 2104691.

J. Biol. Chem., 272(20):13117–13125 (1997) "PMID:9148925, UI:97294720".

NCBI General Identification No. 5455860.

Sugimoto and Suzuki (1996) J. Biochem, 119:500–505.

*Primary Examiner*—Sean McGarry

(57) ABSTRACT

This invention relates to an isolated nucleic acid fragment encoding an alpha-glucosidase II subunit. The invention also relates to the construction of a chimeric gene encoding all or a portion of the alpha-glucosidase II subunit, in sense or antisense orientation, wherein expression of the chimeric gene results in production of altered levels of the alpha-glucosidase II subunit in a transformed host cell.

13 Claims, 3 Drawing Sheets

```
SEQ ID NO:08       ** * ****** *  ****** *********** *** * *** *  * ** **
SEQ ID NO:17   MRNETLRLILLILLCSHLHSVLSWKKEEFRTCHQTPFCKRARSRAPGSSSLIATDVTISH
               MRAPLLLYPLLLLL-LFVTSAYSWKKEEFRNCDQTPFCKRARSRKPGSCNLRVADVSISD
               1                                                           60

SEQ ID NO:08   *** *** ***   * ******** ************* ** **** *********** *
SEQ ID NO:17   GDLTAKLTPKHD---SQSETKPLLLTLSVYQRGILRLKIDEDPSLSPPKKREVPDVIVS
               GDLIAKLVPKEENPESEQPNKPLVLTLSVYQDGVMRKIDEDQNLNPPKKRFEVPEVIEE
               61                                                          120

SEQ ID NO:08   * ******       ** * ******** *  * ** *** ** *** **** * ***
SEQ ID NO:17   EFPSTKLWLPKISSVE----NGLSSSVYLSDGHSAVLRHDPELFIRDDSSGDRVISLNS
               DFLNTKLWLTRVKEEQIDGVSSFSSVFYLSDGYEGVLRHDPFEVFARESGSGKRVLSINS
               121                                                         180

SEQ ID NO:08       ******* * *** ******* ******* ****** ********* **** *
SEQ ID NO:17   HDLFDEEQLKHKSEDDNWEEQFRSHTDRRPYGPQSISFDVSFYGADFVYGIPERAASLAL
               NGLFDFEEQLREKKEGDDWEEKFRSHTDTRPYGPQSISFDVSFYGADFVYGIPEHATSFAL
               181                                                         240

SEQ ID NO:08   *** ***** * ****** **** * ***** ********** ************
SEQ ID NO:17   KPTRGPNVDE-SEPYRLFNLDVFEYIHDSPFGLYGSIPEMVSHGKARGSSGFFWLNAAEM
               KPTKGPNVEEYSEPYRLFNLDVFEYLHESPFGLYGSIPFMISHGKARGSSGFFWLNAAEM
               241                                                         300

SEQ ID NO:08   ****  ** ******  ****  ********* * **** ** *** ** ******
SEQ ID NO:17   QIDVLAPGWDAESG--IALPS--HRIDTEWMSEAGVVDAFFIGPNPKDVLRQYTAVTGT
               QIDVLGSSWNSDESSKIMLPSDKHRIDTLWMSESGVVDTFFFIGPKDVVRQYTSVTGR
               301                                                         360
```

FIG. 1A

```
SEQ ID NO:08        ******  **********   *  ******************************   ****
SEQ ID NO:17    PAMPQLFSIAYHQCRWNYRDEEDVEHVDSKFDELDIPYDVLWLDIEHTDGKRYFTWDRAL
                PSMPQLFATAYHQCRWNYRDEEDVYNVDSKFDEHDIPYDVLWLDIEHTDGKKYFTWDRVL
                361                                                       420

SEQ ID NO:08     **  ******   ****   ***     *  *******    ***** ** *******
SEQ ID NO:17    FPHPEEMQRKLASKGRHMVTIVDPHIKRDENFHLHKEASQKGYYVKDASGNDFDGWCWPG
                FPNPEEMQKKLAAKGRHMVTIVDPHIKRDESYHIPKEALEKGYYVKDATGKDYDGWCWPG
                421                                                       480

SEQ ID NO:08     ****  *  *****  *  **  * ***  **   **********************
SEQ ID NO:17    SSSYPDTLNPEIRSWWADKFSYQSYEGSTPSLYIWNDMNEPSVENGPEVTMPRDVTHYGG
                SSSYTDLLNPEIKSWWSDKFSLDSYVGSTKYLYIWNDMNEPSVENGPEVTMPRDALHHGG
                481                                                       540

SEQ ID NO:08     ******  * ** * ****  ***  *****  *****  ****************
SEQ ID NO:17    VEHRELHNAYGYYFHMATANGLLKRGEGNDRPFVLSRALFAGSQRYGAVWTGDNTADWDH
                VEHRELHNSYGYYFHMGTSDGLLKRGDGKDRPFVLARAFFAGSQRYGAIWTGDNTAEWEH
                541                                                       600

SEQ ID NO:08     ****  **** **** * **  *   ** *********  ** ****** ********
SEQ ID NO:17    LRVSIPMVLTLGLTGMSFSGADIGGFFGNPEPELLVRWYQLGAYYPFFRAHAHHDTKRRE
                LRVSVPMVLTLSISGIVFSGADVGGFFGNPDTELLLVRWYQVGAYYPFFRGHAHHDTKRRE
                601                                                       660
```

FIG. 1B

```
                   ********** *   ******* *       ************** *   ****** ** *****
SEQ ID NO:08       PWLFGERNTELIKDAIHVRYALLPYFYTLFREANTTGVPVVRPLWMEFPSDEATFSNDET
SEQ ID NO:17       PWLFGERNTQLMREAIHVRYMYLPYFYTLFREANSSGTPVARPLWMEFPGDEKSFSNDEA
                   661                                                        720

****  *** ***  * *  ****  ********  *       **  *** **  ****
SEQ ID NO:08       FMVGSSILVQGIYTERAKHASVYLPGKQSWYDLRTGAVYKGGVTHKLEVTEESIPAFQRA
SEQ ID NO:17       FMVGNGLLVQGVYTEKPKHVSVYLPGEESWYDLRSASAYNGGHTHKYEVSEDSIPSFQRA
                   721                                                        780

****  ****  *****  **********  *************  *  **  *   **
SEQ ID NO:08       GTIIARKDREFRRSSTQMANDPYTLVVALNSSQAAEGELYIDDGSSFNFLQGGYIHRRFIF
SEQ ID NO:17       GTIIPRKDRLRRSSTQMENDPYTLVIALNSSKAAEGELYIDDGKSYEFKQGAFILKWEAY
                   781                                                        840

*         *        *     * ******  ******
SEQ ID NO:08       SNGKLTSIDLAPASSSKGRYPSDAFIERIILLGHAPSSKNALIEPSNQKVDIELGPLWVL
SEQ ID NO:17       IFQMPRLQLAVT-----HFPSECTVERIILLLGLSPGAKTALIEPGNKKVEIELGPLFIQ
                   841                                                        900

*  **** *****   **  *  *
SEQ ID NO:08       RARAPAVTTIRRPNVRVAEDWTITVI
SEQ ID NO:17       GNRGS-VPTIRKPNVRITDDWSIQIL
                   901                      926
```

FIG. 1C

SEQUENCE LISTING

```
<160> NUMBER OF SEQ ID NOS: 19

<210> SEQ ID NO 1
<211> LENGTH: 554
<212> TYPE: DNA
<213> ORGANISM: Zea mays
<220> FEATURE:
<221> NAME/KEY: unsure
<222> LOCATION: (189)
<221> NAME/KEY: unsure
<222> LOCATION: (234)
<221> NAME/KEY: unsure
<222> LOCATION: (288)
<221> NAME/KEY: unsure
<222> LOCATION: (298)
<221> NAME/KEY: unsure
<222> LOCATION: (366)
<221> NAME/KEY: unsure
<222> LOCATION: (378)
<221> NAME/KEY: unsure
<222> LOCATION: (392)
<221> NAME/KEY: unsure
<222> LOCATION: (395)
<221> NAME/KEY: unsure
```

```
<222> LOCATION: (398)
<221> NAME/KEY: unsure
<222> LOCATION: (422)
<221> NAME/KEY: unsure
<222> LOCATION: (424)
<221> NAME/KEY: unsure
<222> LOCATION: (441)
<221> NAME/KEY: unsure
<222> LOCATION: (444)
<221> NAME/KEY: unsure
<222> LOCATION: (449)
<221> NAME/KEY: unsure
<222> LOCATION: (451)
<221> NAME/KEY: unsure
<222> LOCATION: (461)
<221> NAME/KEY: unsure
<222> LOCATION: (466)
<221> NAME/KEY: unsure
<222> LOCATION: (473)
<221> NAME/KEY: unsure
<222> LOCATION: (488)
<221> NAME/KEY: unsure
<222> LOCATION: (490)
<221> NAME/KEY: unsure
<222> LOCATION: (503)
<221> NAME/KEY: unsure
<222> LOCATION: (516)..(517)
<221> NAME/KEY: unsure
<222> LOCATION: (532)
<221> NAME/KEY: unsure
<222> LOCATION: (540)
<221> NAME/KEY: unsure
<222> LOCATION: (543)

<400> SEQUENCE: 1
cgcagtccca gatccacccg tctgttccgc cccgccgcgc gcaccatgga tcccccgcgg      60
cggcggctac ccgccgcgct cgtcgtcttc ctcctgctcc tcgccgcggc ctctcccgtc     120
gcgcgcgcgt ggaagaagga cgagtttcgc aactgcaacc agacgcccct ctgcaagcgc     180
gctcggacnc gcgccccgca ctcgctcgac gcgccgctct ccctcgccgc cggntccctg     240
gccgtctccc ccgatggctc tatctccgct gagctctccc acccgtcncg cccgcggncc     300
ctcgtgctcc gcctctctgc gctgccccg cacgcgctgc ggctccagat cgatgaggac     360
tactcnaccg ccacgccngc gcaccgtcgg tncangtncc cgatgtctct cccggaactc     420
angncgcagc tcaacttccc ngancgaana ntggcgctgg ngtatncacg gtncgctctc     480
tcgacatnan gtatcgtata canatcgtcg agctanntcc gcgtgcgggt tngcgatccn     540
tgnatcttac tcaa                                                      554

<210> SEQ ID NO 2
<211> LENGTH: 114
<212> TYPE: PRT
<213> ORGANISM: Zea mays
<220> FEATURE:
<221> NAME/KEY: UNSURE
<222> LOCATION: (85)

<400> SEQUENCE: 2

Met Asp Pro Pro Arg Arg Arg Leu Pro Ala Ala Leu Val Val Phe Leu
 1               5                  10                  15

Leu Leu Leu Ala Ala Ala Ser Pro Val Ala Arg Ala Trp Lys Lys Asp
                20                  25                  30

Glu Phe Arg Asn Cys Asn Gln Thr Pro Phe Cys Lys Arg Ala Arg Thr
            35                  40                  45

Arg Ala Pro His Ser Leu Asp Ala Pro Leu Ser Leu Ala Ala Gly Ser
        50                  55                  60
```

Leu Ala Val Ser Pro Asp Gly Ser Ile Ser Ala Glu Leu Ser His Pro
 65                  70                  75                  80

Ser Arg Pro Arg Xaa Leu Val Leu Arg Leu Ser Ala Leu Pro Pro His
                 85                  90                  95

Ala Leu Arg Leu Gln Ile Asp Glu Asp Tyr Ser Thr Ala Thr Pro Ala
            100                 105                 110

His Arg

<210> SEQ ID NO 3
<211> LENGTH: 503
<212> TYPE: DNA
<213> ORGANISM: Oryza sativa
<220> FEATURE:
<221> NAME/KEY: unsure
<222> LOCATION: (100)
<221> NAME/KEY: unsure
<222> LOCATION: (113)
<221> NAME/KEY: unsure
<222> LOCATION: (165)
<221> NAME/KEY: unsure
<222> LOCATION: (187)
<221> NAME/KEY: unsure
<222> LOCATION: (202)
<221> NAME/KEY: unsure
<222> LOCATION: (217)
<221> NAME/KEY: unsure
<222> LOCATION: (306)..(307)
<221> NAME/KEY: unsure
<222> LOCATION: (309)
<221> NAME/KEY: unsure
<222> LOCATION: (324)
<221> NAME/KEY: unsure
<222> LOCATION: (332)
<221> NAME/KEY: unsure
<222> LOCATION: (375)
<221> NAME/KEY: unsure
<222> LOCATION: (387)
<221> NAME/KEY: unsure
<222> LOCATION: (390)
<221> NAME/KEY: unsure
<222> LOCATION: (397)
<221> NAME/KEY: unsure
<222> LOCATION: (402)
<221> NAME/KEY: unsure
<222> LOCATION: (434)
<221> NAME/KEY: unsure
<222> LOCATION: (442)
<221> NAME/KEY: unsure
<222> LOCATION: (447)
<221> NAME/KEY: unsure
<222> LOCATION: (453)
<221> NAME/KEY: unsure
<222> LOCATION: (466)

<400> SEQUENCE: 3
tgatattcca tatgatgtgc tctggcttga cattgaacac acagatggca agcggtactt      60
tacatgggat cattcagcat ttcctaaccc agaggtgatn caagggaaga tancagataa     120
aggggaggaa gatggtcacc attgtagacc cacatatcaa gcganacatt cgttccacct     180
ccacgangaa tctactgcta anggatacta tgttaanaga tgcgactggg gaaagactcg     240
aatgggttgg tgctggcctg ggggcatccg tccatatcct gacatgttta accccctgaat    300 acgaannant tgtgggctta caantttccc cnaatgaaaa cttacaggat tcaactcccc     360
acatttgtaa acccnggatg accatgnatn accacanect tnaatggccc tgaggtacca    420
tcccaaggat gcanacattt cnggatnttt acnaaaaact gcacanccta cgtacacttc     480
catatgctcc acaaatggtc cta                                             503

```
<210> SEQ ID NO 4
<211> LENGTH: 71
<212> TYPE: PRT
<213> ORGANISM: Oryza sativa
<220> FEATURE:
<221> NAME/KEY: UNSURE
<222> LOCATION: (33)
<221> NAME/KEY: UNSURE
<222> LOCATION: (38)
<221> NAME/KEY: UNSURE
<222> LOCATION: (55)
<221> NAME/KEY: UNSURE
<222> LOCATION: (62)
<221> NAME/KEY: UNSURE
<222> LOCATION: (67)

<400> SEQUENCE: 4

Asp Ile Pro Tyr Asp Val Leu Trp Leu Asp Ile Glu His Thr Asp Gly
  1               5                  10                  15

Lys Arg Tyr Phe Thr Trp Asp His Ser Ala Phe Pro Asn Pro Glu Val
             20                  25                  30

Xaa Gln Gly Lys Ile Xaa Asp Lys Gly Glu Glu Asp Gly His His Cys
         35                  40                  45

Arg Pro Thr Tyr Gln Ala Xaa His Ser Phe His Leu His Xaa Glu Ser
     50                  55                  60

Thr Ala Xaa Gly Tyr Tyr Val
 65                  70

<210> SEQ ID NO 5
<211> LENGTH: 523
<212> TYPE: DNA
<213> ORGANISM: Glycine max
<220> FEATURE:
<221> NAME/KEY: unsure
<222> LOCATION: (313)
<221> NAME/KEY: unsure
<222> LOCATION: (404)
<221> NAME/KEY: unsure
<222> LOCATION: (427)
<221> NAME/KEY: unsure
<222> LOCATION: (450)
<221> NAME/KEY: unsure
<222> LOCATION: (522)

<400> SEQUENCE: 5
gagagagaga ggactagttc tctctctcca cagcgagaag aagatgagga acgaaacgct     60
gcgtttgatc cttctcctcc tcctctgttc ccaccttcac tccgtcctct catgaagaa    120 agaggagttc cgaacctgcc accaaacacc attctgcaag cgcgcccgat ccgcgcccc    180 cggctcctcc tccctcatcg ccaccgacgt taccatctcc cacggcgacc tcaccgccaa    240 actcaccccca aaacatgatt ctcaatccga aaccaaaccc ttactcctca ccctctccgt    300
ctaccaacgc ggnatcctcc ggctcaagat tgatgaggga cccttccctc tccctccca    360 aagaaaacgc ttcgagggtc cccgacgtca atcgttttcc gaanttccct ccaacaaagg    420
tctgggntcc ccaaaatcct ccctccggtn agaaaaacgg ctctcctcc tccggtttta    480 actcctccga agggtcaatt ccggccggtt cctccggcaa ang                       523

<210> SEQ ID NO 6
<211> LENGTH: 110
<212> TYPE: PRT
<213> ORGANISM: Glycine max
<220> FEATURE:
<221> NAME/KEY: UNSURE
<222> LOCATION: (74)
<221> NAME/KEY: UNSURE
```

<222> LOCATION: (102)

<400> SEQUENCE: 6

```
Met Arg Asn Glu Thr Leu Arg Leu Ile Leu Leu Leu Leu Cys Ser
 1               5                  10                  15

His Leu His Ser Val Leu Ser Trp Lys Lys Glu Glu Phe Arg Thr Cys
            20                  25                  30

His Gln Thr Pro Phe Cys Lys Arg Ala Arg Ser Arg Ala Pro Gly Ser
        35                  40                  45

Ser Ser Leu Ile Ala Thr Asp Val Thr Ile Ser His Gly Asp Leu Thr
    50                  55                  60

Ala Lys Leu Thr Pro Lys His Asp Ser Xaa Asp Ser Gln Ser Glu Thr
65                  70                  75                  80

Lys Pro Leu Leu Leu Thr Leu Ser Val Tyr Gln Arg Gly Ile Leu Arg
                85                  90                  95

Leu Lys Ile Asp Glu Xaa Pro Ser Leu Ser Pro Pro Lys Glu
                100                 105                 110
```

<210> SEQ ID NO 7
<211> LENGTH: 3159
<212> TYPE: DNA
<213> ORGANISM: Glycine max

<400> SEQUENCE: 7

| | | | | | |
|---|---|---|---|---|---|
| gcacgaggag | agagagagga | ctagttctct | ctctccacag | cgagaagaag | atgaggaacg | 60 |
| aaacgctgcg | tttgatcctt | ctcctcctcc | tctgttccca | ccttcactcc | gtcctctcat | 120 |
| ggaagaaaga | ggagttccga | acctgccacc | aaacaccatt | ctgcaagcgc | gcccgatccc | 180 |
| gcgcccccgg | ctcctcctcc | ctcatcgcca | ccgacgttac | catctcccac | ggcgacctca | 240 |
| ccgccaaact | caccccaaaa | catgattctc | aatccgaaac | caaacccta | ctcctcaccc | 300 |
| tctccgtcta | ccaacgcggc | atcctccgcc | tcaagatcga | tgaggaccct | tccctctccc | 360 |
| ctcccaagaa | acgcttcgag | gtccccgacg | tcatcgtttc | cgaattcccc | tccaccaagc | 420 |
| tctggctccc | caaaatctcc | tccgtagaaa | acggcctctc | ctcctccgtt | acctctccg | 480 |
| acggtcattc | cgccgtcctc | cgccacgacc | ccttcgaact | cttcatccgc | gacgactcgt | 540 |
| ccggcgaccg | cgtcatctcc | ctcaactccc | atgacctctt | cgacttcgag | cagctcaaac | 600 |
| acaaatccga | agacgataac | tgggaagaac | aattccgatc | ccacaccgac | cgtagaccct | 660 |
| acggccccca | atccatctcc | ttcgacgttt | ccttctacgg | cgccgatttc | gtttacggca | 720 |
| tccccgaacg | tgccgcaagt | cttgccctaa | agcccaccag | aggcccaaac | gtcgacgaat | 780 |
| ctgagcccta | ccgcctcttc | aacctcgacg | tcttcgagta | catccacgat | tccccttcg | 840 |
| gcctctacgg | ttccattccc | ttcatggttt | ctcacgggaa | agccagggga | agttccgggt | 900 |
| ttttctggct | caacgccgcc | gagatgcaga | ttgacgttct | tgcccctggc | tgggacgccg | 960 |
| agtccggcat | agcgctccct | tcgcaccgaa | tcgacacgtt | ttggatgagc | gaggctggtg | 1020 |
| ttgtggacgc | tttcttttc | atcggtccga | accctaagga | tgtgctgaga | cagtacacgg | 1080 |
| cggtgacggg | aactccggcg | atgccgcagc | tgttttcgat | tgcgtaccac | cagtgccggt | 1140 |
| ggaattatcg | cgatgaggag | gatgttgagc | atgtggattc | caagtttgat | gagttggata | 1200 |
| ttccttatga | tgtgttgtgg | cttgacattg | agcacactga | tgggaagagg | tatttacttt | 1260 |
| gggatagggc | tcttttcccc | caccctgagg | agatgcagag | gaagttggct | tctaaaggga | 1320 |
| ggcacatggt | gaccattgtg | gatcctcaca | ttaagcggga | cgagaatttt | catttgcaca | 1380 |

-continued

```
aggaggcctc tcagaagggg tattatgtta aggatgccag tgggaatgac tttgatggct    1440
ggtgctggcc gggttcgtca tcatatccgg atactttgaa cccggaaatt aggtcctggt    1500
gggctgataa gttctcttac cagagttatg agggttccac gccttctctt tacatatgga    1560
atgacatgaa tgaaccttct gtcttcaatg ggcctgaggt gacaatgcct agagatgtta    1620
cacactatgg aagtgtggaa catcgggagt tgcacaatgc ctatggatat tacttccaca    1680
tggcgaccgc taatgggcta ctgaagcgtg gtgagggaa tgacaggcca tttgttttat     1740
caagagcatt atttgctgga agtcaaaggt atggagcagt ttggactggg ataacactg     1800 ctgattggga tcacctaaga gtttctatcc caatggtttt gacccttggt cttactggga    1860
tgtcattctc tggtgctgat attggtggat tttttgggaa tcctgaacct gagttattgg    1920
ttcggtggta tcagctagga gcttactatc ctttctttag ggcccacgcc catcacgaca    1980
caaaaagacg agaaccatgg ttgtttggag aacgaaatac agaattgatt aaggatgcaa    2040
tacatgttcg ttatgcactt ctcccgtatt tctacacatt attcagggag ctaacacta    2100 caggtgttcc tgtggtccgt ccattgtgga tggaattccc atctgatgaa gctacttta    2160 gcaatgacga aactttcatg gttgggagca gtattttagt tcaagggatc tatacagagc    2220
gagctaagca tgcatcagtc tatttgcctg gaaaacaatc ctggtatgac ctaagaactg    2280
gagctgtgta caagggaggg gtgacacaca gttggaggt tacagaggag agcattcctg    2340
ctttccagag agctggaacc attattgcaa ggaaagaccg gtttcggcga agttccactc    2400
agatggcaaa tgatccctac actctggttg tagctctgaa tagttcccaa gcagctgagg    2460
gtgaactcta catagatgat ggcagcagct ttaattttct gcaagggggc tatatccata    2520
gacgatttat tttctcgaat gggaaactta cttctataga cctggcacct gcttccagta    2580
gcaaggggcg ttatccatca gatgctttca ttgagaggat tatcctgctg ggacatgctc    2640
ctagctcaaa aaatgcactc attgagccat caaatcaaaa ggttgatatt gaacttggcc    2700 cccttgggt tctaagggct cgtgcaccag ctgttacaac catacgtaga cctaatgttc     2760
gtgttgcaga agattggact ataacagtta tataacattt ccggttcgag ggaggagttt    2820
aatgttcaaa gttactgcta gtgcacaacg agattttgtt tctgtagttg agttgatatg    2880
aagttcagct gcaacgttgg ggtaagaaga agaaaatca ttaattttga agaatgcatt     2940
tgcaccaact cagtttgagc ggcttattta atgtaggact cgttgactgg aaagatttaa    3000
catttggaag ttgtgattcc attgttgtct actattttga taaggataaa tttgtatcgt    3060
ctggaatggt ctgtcttggg aaaagcttgt gatgaatgca ataacttagt cgttagttta    3120
aaaaaaaaaa aaaaaaaaaa aaaaaaaaaa aaaaaaaa                            3159
```

<210> SEQ ID NO 8
<211> LENGTH: 914
<212> TYPE: PRT
<213> ORGANISM: Glycine max

<400> SEQUENCE: 8

```
Met Arg Asn Glu Thr Leu Arg Leu Ile Leu Leu Leu Leu Cys Ser
  1               5                  10                  15

His Leu His Ser Val Leu Ser Trp Lys Lys Glu Glu Phe Arg Thr Cys
                 20                  25                  30

His Gln Thr Pro Phe Cys Lys Arg Ala Arg Ser Arg Ala Pro Gly Ser
             35                  40                  45

Ser Ser Leu Ile Ala Thr Asp Val Thr Ile Ser His Gly Asp Leu Thr
         50                  55                  60
```

-continued

```
Ala Lys Leu Thr Pro Lys His Asp Ser Gln Ser Glu Thr Lys Pro Leu
 65                  70                  75                  80

Leu Leu Thr Leu Ser Val Tyr Gln Arg Gly Ile Leu Arg Leu Lys Ile
                 85                  90                  95

Asp Glu Asp Pro Ser Leu Ser Pro Pro Lys Lys Arg Phe Glu Val Pro
            100                 105                 110

Asp Val Ile Val Ser Glu Phe Pro Ser Thr Lys Leu Trp Leu Pro Lys
            115                 120                 125

Ile Ser Ser Val Glu Asn Gly Leu Ser Ser Val Tyr Leu Ser Asp
    130                 135                 140

Gly His Ser Ala Val Leu Arg His Asp Pro Phe Glu Leu Phe Ile Arg
145                 150                 155                 160

Asp Asp Ser Ser Gly Asp Arg Val Ile Ser Leu Asn Ser His Asp Leu
                165                 170                 175

Phe Asp Phe Glu Gln Leu Lys His Lys Ser Glu Asp Asp Asn Trp Glu
            180                 185                 190

Glu Gln Phe Arg Ser His Thr Asp Arg Arg Pro Tyr Gly Pro Gln Ser
        195                 200                 205

Ile Ser Phe Asp Val Ser Phe Tyr Gly Ala Asp Phe Val Tyr Gly Ile
    210                 215                 220

Pro Glu Arg Ala Ala Ser Leu Ala Leu Lys Pro Thr Arg Gly Pro Asn
225                 230                 235                 240

Val Asp Glu Ser Glu Pro Tyr Arg Leu Phe Asn Leu Asp Val Phe Glu
            245                 250                 255

Tyr Ile His Asp Ser Pro Phe Gly Leu Tyr Gly Ser Ile Pro Phe Met
            260                 265                 270

Val Ser His Gly Lys Ala Arg Gly Ser Ser Gly Phe Phe Trp Leu Asn
        275                 280                 285

Ala Ala Glu Met Gln Ile Asp Val Leu Ala Pro Gly Trp Asp Ala Glu
        290                 295                 300

Ser Gly Ile Ala Leu Pro Ser His Arg Ile Asp Thr Phe Trp Met Ser
305                 310                 315                 320

Glu Ala Gly Val Val Asp Ala Phe Phe Phe Ile Gly Pro Asn Pro Lys
                325                 330                 335

Asp Val Leu Arg Gln Tyr Thr Ala Val Thr Gly Thr Pro Ala Met Pro
            340                 345                 350

Gln Leu Phe Ser Ile Ala Tyr His Gln Cys Arg Trp Asn Tyr Arg Asp
        355                 360                 365

Glu Glu Asp Val Glu His Val Asp Ser Lys Phe Asp Glu Leu Asp Ile
    370                 375                 380

Pro Tyr Asp Val Leu Trp Leu Asp Ile Glu His Thr Asp Gly Lys Arg
385                 390                 395                 400

Tyr Phe Thr Trp Asp Arg Ala Leu Phe Pro His Pro Glu Glu Met Gln
                405                 410                 415

Arg Lys Leu Ala Ser Lys Gly Arg His Met Val Thr Ile Val Asp Pro
            420                 425                 430

His Ile Lys Arg Asp Glu Asn Phe His Leu His Lys Glu Ala Ser Gln
        435                 440                 445

Lys Gly Tyr Tyr Val Lys Asp Ala Ser Gly Asn Asp Phe Asp Gly Trp
    450                 455                 460

Cys Trp Pro Gly Ser Ser Ser Tyr Pro Asp Thr Leu Asn Pro Glu Ile
465                 470                 475                 480
```

-continued

```
Arg Ser Trp Trp Ala Asp Lys Phe Ser Tyr Gln Ser Tyr Glu Gly Ser
                485                 490                 495

Thr Pro Ser Leu Tyr Ile Trp Asn Asp Met Asn Glu Pro Ser Val Phe
            500                 505                 510

Asn Gly Pro Glu Val Thr Met Pro Arg Asp Val Thr His Tyr Gly Gly
            515                 520                 525

Val Glu His Arg Glu Leu His Asn Ala Tyr Gly Tyr Tyr Phe His Met
    530                 535                 540

Ala Thr Ala Asn Gly Leu Leu Lys Arg Gly Glu Gly Asn Asp Arg Pro
545                 550                 555                 560

Phe Val Leu Ser Arg Ala Leu Phe Ala Gly Ser Gln Arg Tyr Gly Ala
                565                 570                 575

Val Trp Thr Gly Asp Asn Thr Ala Asp Trp Asp His Leu Arg Val Ser
            580                 585                 590

Ile Pro Met Val Leu Thr Leu Gly Leu Thr Gly Met Ser Phe Ser Gly
            595                 600                 605

Ala Asp Ile Gly Gly Phe Phe Gly Asn Pro Glu Pro Glu Leu Leu Val
610                 615                 620

Arg Trp Tyr Gln Leu Gly Ala Tyr Tyr Pro Phe Phe Arg Ala His Ala
625                 630                 635                 640

His His Asp Thr Lys Arg Arg Glu Pro Trp Leu Phe Gly Glu Arg Asn
                645                 650                 655

Thr Glu Leu Ile Lys Asp Ala Ile His Val Arg Tyr Ala Leu Leu Pro
            660                 665                 670

Tyr Phe Tyr Thr Leu Phe Arg Glu Ala Asn Thr Thr Gly Val Pro Val
            675                 680                 685

Val Arg Pro Leu Trp Met Glu Phe Pro Ser Asp Glu Ala Thr Phe Ser
    690                 695                 700

Asn Asp Glu Thr Phe Met Val Gly Ser Ser Ile Leu Val Gln Gly Ile
705                 710                 715                 720

Tyr Thr Glu Arg Ala Lys His Ala Ser Val Tyr Leu Pro Gly Lys Gln
                725                 730                 735

Ser Trp Tyr Asp Leu Arg Thr Gly Ala Val Tyr Lys Gly Gly Val Thr
            740                 745                 750

His Lys Leu Glu Val Thr Glu Ser Ile Pro Ala Phe Gln Arg Ala
    755                 760                 765

Gly Thr Ile Ile Ala Arg Lys Asp Arg Phe Arg Arg Ser Ser Thr Gln
770                 775                 780

Met Ala Asn Asp Pro Tyr Thr Leu Val Val Ala Leu Asn Ser Ser Gln
785                 790                 795                 800

Ala Ala Glu Gly Glu Leu Tyr Ile Asp Asp Gly Ser Ser Phe Asn Phe
                805                 810                 815

Leu Gln Gly Gly Tyr Ile His Arg Phe Ile Phe Ser Asn Gly Lys
            820                 825                 830

Leu Thr Ser Ile Asp Leu Ala Pro Ala Ser Ser Lys Gly Arg Tyr
            835                 840                 845

Pro Ser Asp Ala Phe Ile Glu Arg Ile Ile Leu Leu Gly His Ala Pro
850                 855                 860

Ser Ser Lys Asn Ala Leu Ile Glu Pro Ser Asn Gln Lys Val Asp Ile
865                 870                 875                 880

Glu Leu Gly Pro Leu Trp Val Leu Arg Ala Arg Ala Pro Ala Val Thr
                885                 890                 895

Thr Ile Arg Arg Pro Asn Val Arg Val Ala Glu Asp Trp Thr Ile Thr
```

-continued

```
                900                 905                 910
Val Ile

<210> SEQ ID NO 9
<211> LENGTH: 491
<212> TYPE: DNA
<213> ORGANISM: Triticum aestivum
<220> FEATURE:
<221> NAME/KEY: unsure
<222> LOCATION: (222)
<221> NAME/KEY: unsure
<222> LOCATION: (305)
<221> NAME/KEY: unsure
<222> LOCATION: (361)
<221> NAME/KEY: unsure
<222> LOCATION: (419)
<221> NAME/KEY: unsure
<222> LOCATION: (423)
<221> NAME/KEY: unsure
<222> LOCATION: (430)
<221> NAME/KEY: unsure
<222> LOCATION: (454)
<221> NAME/KEY: unsure
<222> LOCATION: (465)..(466)..(467)
<221> NAME/KEY: unsure
<222> LOCATION: (484)

<400> SEQUENCE: 9
gcaatacata tgcggtattc attgttgccc tactattact ctctgttcca agaggctagt     60
gtaactggtg ttcctgttat gcgtcctttg tggttggaat ttcctgacga caaggaaaca    120
tataataatg gtgaggcttt tatggttggg ccaagcattt tggcccaagg aatttacgaa    180
gagggccaga aatcagtgtc ggtttacctt cctgggaacg gngttatggt atgacttgag    240
aaatggatct ccatacaagg gaagtgtgtc acacaagctg caagtttcag aagatagcat    300
accangcttc caaaggtccg gcacaattgt gccaagaaag gatagattca ggcgcattct    360
nactcaagat ggtgaacgat tcatacaccc tggtgatagg cctcaataac tcctgggtnc    420
tcnacaaggn gacttatgtg gatgatggga aaantatgat ttcannnagg gcatcaacca    480
tcgnggtttg t                                                         491

<210> SEQ ID NO 10
<211> LENGTH: 150
<212> TYPE: PRT
<213> ORGANISM: Triticum aestivum
<220> FEATURE:
<221> NAME/KEY: UNSURE
<222> LOCATION: (73)..(74)
<221> NAME/KEY: UNSURE
<222> LOCATION: (102)
<221> NAME/KEY: UNSURE
<222> LOCATION: (123)
<221> NAME/KEY: UNSURE
<222> LOCATION: (141)
<221> NAME/KEY: UNSURE
<222> LOCATION: (143)

<400> SEQUENCE: 10

Ala Ile His Met Arg Tyr Ser Leu Leu Pro Tyr Tyr Ser Leu Phe
 1               5                  10                  15

Gln Glu Ala Ser Val Thr Gly Val Pro Val Met Arg Pro Leu Trp Leu
            20                  25                  30

Glu Phe Pro Asp Asp Lys Glu Thr Tyr Asn Asn Gly Glu Ala Phe Met
        35                  40                  45

Val Gly Pro Ser Ile Leu Ala Gln Gly Ile Tyr Glu Glu Gly Gln Lys
    50                  55                  60
```

Ser Val Ser Val Tyr Leu Pro Gly Xaa Xaa Leu Trp Tyr Asp Leu Arg
 65                  70                  75                  80

Asn Gly Ser Pro Tyr Lys Gly Ser Val Ser His Lys Leu Gln Val Ser
             85                  90                  95

Glu Asp Ser Ile Pro Xaa Phe Gln Arg Ser Gly Thr Ile Val Pro Arg
            100                 105                 110

Lys Asp Arg Phe Arg Arg Ile Leu Thr Gln Xaa Val Asn Asp Ser Tyr
        115                 120                 125

Thr Leu Val Ile Gly Leu Asn Asn Ser Trp Val Leu Xaa Lys Xaa Thr
    130                 135                 140

Tyr Val Asp Asp Gly Lys
145                 150

<210> SEQ ID NO 11
<211> LENGTH: 566
<212> TYPE: DNA
<213> ORGANISM: Zea mays
<220> FEATURE:
<221> NAME/KEY: unsure
<222> LOCATION: (387)

<400> SEQUENCE: 11
aagatgaaga gtttgatcat gagtcagaag atgaatatgt tgatgaccat gatgagcatg     60
ttgagtccta taaatctgat gatgaccaga aagatttaac tgagccagga catgcatcgt    120
ggttggacaa aattcagcag actgtacaga atgttttcca aaaattcaac ttttttagga    180
cccctgtaga tttgtcagag gcttctcgtg ttcgtaagga gtatgacgat gccaactcaa    240
agctttcaaa aattcagtct aagatatcca atttagctga aagctaaaa catgattttg     300 gcaaagacaa ggagttctat tccttttatg atcagtgctt tgagaccaag gaaggaaagt    360
atacttacaa ggtctgtgca tataagnagc atcacaggtg aagggcacag ttccaccaac    420
ctggggagat gggacaattt gaagaatcgt acagagtatg cacttttcag tgagacaatg    480
ctggaatgtc tgaccgagcc taaggtaggc ttgatgtggc tgacaatgac ttaatgcgtg    540
atgagctgca gatgcgagta tgtgct                                         566

<210> SEQ ID NO 12
<211> LENGTH: 127
<212> TYPE: PRT
<213> ORGANISM: Zea mays

<400> SEQUENCE: 12

Glu Glu Phe Asp His Glu Ser Glu Asp Glu Tyr Val Asp Asp His Asp
 1               5                  10                  15

Glu His Val Glu Ser Tyr Lys Ser Asp Asp Gln Lys Asp Leu Thr
             20                  25                  30

Glu Pro Gly His Ala Ser Trp Leu Asp Lys Ile Gln Gln Thr Val Gln
         35                  40                  45

Asn Val Phe Gln Lys Phe Asn Phe Phe Arg Thr Pro Val Asp Leu Ser
     50                  55                  60

Glu Ala Ser Arg Val Arg Lys Glu Tyr Asp Asp Ala Asn Ser Lys Leu
 65                  70                  75                  80

Ser Lys Ile Gln Ser Lys Ile Ser Asn Leu Ala Glu Lys Leu Lys His
             85                  90                  95

Asp Phe Gly Lys Asp Lys Glu Tyr Ser Phe Tyr Asp Gln Cys Phe
            100                 105                 110

Glu Thr Lys Glu Gly Lys Tyr Thr Tyr Lys Val Cys Ala Tyr Lys
            115                 120                 125

<210> SEQ ID NO 13
<211> LENGTH: 546
<212> TYPE: DNA
<213> ORGANISM: Triticum aestivum
<220> FEATURE:
<221> NAME/KEY: unsure
<222> LOCATION: (364)
<221> NAME/KEY: unsure
<222> LOCATION: (410)
<221> NAME/KEY: unsure
<222> LOCATION: (415)
<221> NAME/KEY: unsure
<222> LOCATION: (459)
<221> NAME/KEY: unsure
<222> LOCATION: (465)
<221> NAME/KEY: unsure
<222> LOCATION: (477)
<221> NAME/KEY: unsure
<222> LOCATION: (507)
<221> NAME/KEY: unsure
<222> LOCATION: (544)

<400> SEQUENCE: 13
acaaggtctg tccatacaag aaagcttcac aggttgaagg acacagttcc actaacctgg      60
ggcgctggga caaatttgaa gaatcctgca ggatgatgca cttttcaaat ggagacaaat     120
gctggaatgg ccctgaccga agcctaaagg tcaggcttag atgtgggctg agcaacgagc     180
ttaacggtgt cgatgagccc agcagatgcg agtatgtcgc tgtactgtca actcctgcaa     240
tgtgtgttga agagaagctg aaggagctgc aacagaaact cgacgctgcg tcttcagacc     300
tgtccggcca cgacgagctc taaactgtca cgaggaaaca atgactccac tattacaacc     360
atancataag aaagaacgct accgagtgat agatagaaag ctggactgtn atgtnccgca     420
aacagcgtag tctggctagg gaaaatttga caaatggcna tggtnaaatt cacacanctg     480
atttatactc acgggtacct ttctttntcc ttgcgggctt tcccaattgt tacaggcact     540
aaanaa                                                                546

<210> SEQ ID NO 14
<211> LENGTH: 83
<212> TYPE: PRT
<213> ORGANISM: Triticum aestivum

<400> SEQUENCE: 14

Lys Val Cys Pro Tyr Lys Lys Ala Ser Gln Val Gly His Ser Ser
 1               5                  10                  15

Thr Asn Leu Gly Arg Trp Asp Lys Phe Glu Ser Cys Arg Met Met
                20                  25                  30

His Phe Ser Asn Gly Asp Lys Cys Trp Asn Gly Pro Asp Arg Ser Leu
            35                  40                  45

Lys Val Arg Leu Arg Cys Gly Leu Ser Asn Glu Leu Asn Gly Val Asp
        50                  55                  60

Glu Pro Ser Arg Cys Glu Tyr Val Ala Val Leu Ser Thr Pro Ala Met
 65                 70                  75                  80

Cys Val Glu

<210> SEQ ID NO 15
<211> LENGTH: 732
<212> TYPE: DNA
<213> ORGANISM: Triticum aestivum -continued

```
<400> SEQUENCE: 15
gcacgagaca aggtctgtcc atacaagaaa gcttcacagg ttgaaggaca cagttccact    60
aacctgggc gctgggacaa atttgaagaa tcctgcagga tgatgcactt ttcaaatgga    120
gacaaatgct ggaatggccc tgaccgaagc ctaaaggtca ggcttagatg tgggctgagc   180
aacgagctta acggtgtcga tgagcccagc agatgcgagt atgtcgctgt actgtcaact   240
cctgcaatgt gtgttgaaga aagctgaag gagctgcaac agaaactcga cgctgcgtct    300
tcagacctgt ccggccacga cgagctctaa actgtcacga ggaaacaatg actccactat   360
tacaaccata accataagaa agaacggcta ccgaggtgga tagatagaaa agcctggagc   420
tgtgagtgta gccgccaaag cagcgttagt ctggctaggg aaaatttga gcaaagtggt    480
cgaatggttg aaattttcac atcatcctga ttttagtagc tgcaactggg tatcttttc    540
ttttagttcc tttgacggac gtttcctcaa attgtttatc taggtcatct gaaagagacc   600
aagccttctg tttgtaactt atcagttatg cacagcgtct ctgaattata cgaagtaata   660
cttttatcgt gtggagtaat acttttacct atacctgcac ataaaaaaaa aaaaaaaaa    720
aaaaaaaaaa aa                                                       732
```

```
<210> SEQ ID NO 16
<211> LENGTH: 109
<212> TYPE: PRT
<213> ORGANISM: Triticum aestivum

<400> SEQUENCE: 16
```

| | | | | | | | | | | | | | | | |
|---|---|---|---|---|---|---|---|---|---|---|---|---|---|---|---|
| Ala | Arg | Asp | Lys | Val | Cys | Pro | Tyr | Lys | Lys | Ala | Ser | Gln | Val | Glu | Gly |
| 1 | | | | 5 | | | | | 10 | | | | | 15 | |
| His | Ser | Ser | Thr | Asn | Leu | Gly | Arg | Trp | Asp | Lys | Phe | Glu | Glu | Ser | Cys |
| | | | 20 | | | | | 25 | | | | | 30 | | |
| Arg | Met | Met | His | Phe | Ser | Asn | Gly | Asp | Lys | Cys | Trp | Asn | Gly | Pro | Asp |
| | | 35 | | | | | 40 | | | | | 45 | | | |
| Arg | Ser | Leu | Lys | Val | Arg | Leu | Arg | Cys | Gly | Leu | Ser | Asn | Glu | Leu | Asn |
| | 50 | | | | | 55 | | | | | 60 | | | | |
| Gly | Val | Asp | Glu | Pro | Ser | Arg | Cys | Glu | Tyr | Val | Ala | Val | Leu | Ser | Thr |
| 65 | | | | | 70 | | | | | 75 | | | | | 80 |
| Pro | Ala | Met | Cys | Val | Glu | Glu | Lys | Leu | Lys | Glu | Leu | Gln | Gln | Lys | Leu |
| | | | 85 | | | | | 90 | | | | | 95 | | |
| Asp | Ala | Ala | Ser | Ser | Asp | Leu | Ser | Gly | His | Asp | Glu | Leu | | | |
| | | | 100 | | | | | 105 | | | | | | | |

```
<210> SEQ ID NO 17
<211> LENGTH: 919
<212> TYPE: PRT
<213> ORGANISM: Solanum tuberosum

<400> SEQUENCE: 17
```

| | | | | | | | | | | | | | | | |
|---|---|---|---|---|---|---|---|---|---|---|---|---|---|---|---|
| Met | Arg | Ala | Pro | Leu | Leu | Leu | Tyr | Pro | Leu | Leu | Leu | Leu | Leu | Leu | Phe |
| 1 | | | | 5 | | | | | 10 | | | | | 15 | |
| Val | Thr | Ser | Ala | Tyr | Ser | Trp | Lys | Lys | Glu | Glu | Phe | Arg | Asn | Cys | Asp |
| | | | 20 | | | | | 25 | | | | | 30 | | |
| Gln | Thr | Pro | Phe | Cys | Lys | Arg | Ala | Arg | Ser | Arg | Lys | Pro | Gly | Ser | Cys |
| | | 35 | | | | | 40 | | | | | 45 | | | |
| Asn | Leu | Arg | Val | Ala | Asp | Val | Ser | Ile | Ser | Asp | Gly | Asp | Leu | Ile | Ala |
| | 50 | | | | | 55 | | | | | 60 | | | | |
| Lys | Leu | Val | Pro | Lys | Glu | Glu | Asn | Pro | Glu | Ser | Glu | Gln | Pro | Asn | Lys |
| 65 | | | | | 70 | | | | | 75 | | | | | 80 |

```
Pro Leu Val Leu Thr Leu Ser Val Tyr Gln Asp Gly Val Met Arg Val
                    85              90                  95
Lys Ile Asp Glu Asp Gln Asn Leu Asn Pro Pro Lys Lys Arg Phe Glu
                100             105             110
Val Pro Glu Val Ile Glu Glu Asp Phe Leu Asn Thr Lys Leu Trp Leu
            115             120             125
Thr Arg Val Lys Glu Glu Gln Ile Asp Gly Val Ser Ser Phe Ser Ser
        130             135             140
Val Phe Tyr Leu Ser Asp Gly Tyr Glu Gly Val Leu Arg His Asp Pro
145             150             155                         160
Phe Glu Val Phe Ala Arg Glu Ser Gly Ser Gly Lys Arg Val Leu Ser
                165             170             175
Ile Asn Ser Asn Gly Leu Phe Asp Phe Glu Gln Leu Arg Glu Lys Lys
                180             185             190
Glu Gly Asp Asp Trp Glu Lys Phe Arg Ser His Thr Asp Thr Arg
        195             200             205
Pro Tyr Gly Pro Gln Ser Ile Ser Phe Asp Val Ser Phe Tyr Gly Ala
        210             215             220
Asp Phe Val Tyr Gly Ile Pro Glu His Ala Thr Ser Phe Ala Leu Lys
225             230             235             240
Pro Thr Lys Gly Pro Asn Val Glu Glu Tyr Ser Glu Pro Tyr Arg Leu
                245             250             255
Phe Asn Leu Asp Val Phe Glu Tyr Leu His Glu Ser Pro Phe Gly Leu
                260             265             270
Tyr Gly Ser Ile Pro Phe Met Ile Ser His Gly Lys Ala Arg Gly Ser
        275             280             285
Ser Gly Phe Phe Trp Leu Asn Ala Ala Glu Met Gln Ile Asp Val Leu
        290             295             300
Gly Ser Gly Trp Asn Ser Asp Glu Ser Ser Lys Ile Met Leu Pro Ser
305             310             315                         320
Asp Lys His Arg Ile Asp Thr Leu Trp Met Ser Glu Ser Gly Val Val
                325             330             335
Asp Thr Phe Phe Phe Ile Gly Pro Gly Pro Lys Asp Val Val Arg Gln
                340             345             350
Tyr Thr Ser Val Thr Gly Arg Pro Ser Met Pro Gln Leu Phe Ala Thr
        355             360             365
Ala Tyr His Gln Cys Arg Trp Asn Tyr Arg Asp Glu Glu Asp Val Tyr
        370             375             380
Asn Val Asp Ser Lys Phe Asp Glu His Asp Ile Pro Tyr Asp Val Leu
385             390             395             400
Trp Leu Asp Ile Glu His Thr Asp Gly Lys Lys Tyr Phe Thr Trp Asp
                405             410             415
Arg Val Leu Phe Pro Asn Pro Glu Glu Met Gln Lys Lys Leu Ala Ala
                420             425             430
Lys Gly Arg His Met Val Thr Ile Val Asp Pro His Ile Lys Arg Asp
        435             440             445
Glu Ser Tyr His Ile Pro Lys Glu Ala Leu Glu Lys Gly Tyr Tyr Val
        450             455             460
Lys Asp Ala Thr Gly Lys Asp Tyr Asp Gly Trp Cys Trp Pro Gly Ser
465             470             475             480
Ser Ser Tyr Thr Asp Leu Leu Asn Pro Glu Ile Lys Ser Trp Trp Ser
                485             490             495
```

-continued

```
Asp Lys Phe Ser Leu Asp Ser Tyr Val Gly Ser Thr Lys Tyr Leu Tyr
            500                 505                 510
Ile Trp Asn Asp Met Asn Glu Pro Ser Val Phe Asn Gly Pro Glu Val
            515                 520                 525
Thr Met Pro Arg Asp Ala Leu His His Gly Val Glu His Arg Glu
        530                 535                 540
Leu His Asn Ser Tyr Gly Tyr Tyr Phe His Met Gly Thr Ser Asp Gly
545                 550                 555                 560
Leu Leu Lys Arg Gly Asp Gly Lys Asp Arg Pro Phe Val Leu Ala Arg
                565                 570                 575
Ala Phe Phe Ala Gly Ser Gln Arg Tyr Gly Ala Ile Trp Thr Gly Asp
            580                 585                 590
Asn Thr Ala Glu Trp Glu His Leu Arg Val Ser Val Pro Met Val Leu
            595                 600                 605
Thr Leu Ser Ile Ser Gly Ile Val Phe Ser Gly Ala Asp Val Gly Gly
        610                 615                 620
Phe Phe Gly Asn Pro Asp Thr Glu Leu Leu Val Arg Trp Tyr Gln Val
625                 630                 635                 640
Gly Ala Tyr Tyr Pro Phe Phe Arg Gly His Ala His His Asp Thr Lys
                645                 650                 655
Arg Arg Glu Pro Trp Leu Phe Gly Glu Arg Asn Thr Gln Leu Met Arg
            660                 665                 670
Glu Ala Ile His Val Arg Tyr Met Tyr Leu Pro Tyr Phe Tyr Thr Leu
            675                 680                 685
Phe Arg Glu Ala Asn Ser Ser Gly Thr Pro Val Ala Arg Pro Leu Trp
        690                 695                 700
Met Glu Phe Pro Gly Asp Glu Lys Ser Phe Ser Asn Asp Glu Ala Phe
705                 710                 715                 720
Met Val Gly Asn Gly Leu Leu Val Gln Gly Val Tyr Thr Glu Lys Pro
                725                 730                 735
Lys His Val Ser Val Tyr Leu Pro Gly Glu Glu Ser Trp Tyr Asp Leu
            740                 745                 750
Arg Ser Ala Ser Ala Tyr Asn Gly Gly His Thr His Lys Tyr Glu Val
            755                 760                 765
Ser Glu Asp Ser Ile Pro Ser Phe Gln Arg Ala Gly Thr Ile Ile Pro
        770                 775                 780
Arg Lys Asp Arg Leu Arg Arg Ser Ser Thr Gln Met Glu Asn Asp Pro
785                 790                 795                 800
Tyr Thr Leu Val Ile Ala Leu Asn Ser Ser Lys Ala Ala Glu Gly Glu
                805                 810                 815
Leu Tyr Ile Asp Asp Gly Lys Ser Tyr Glu Phe Lys Gln Gly Ala Phe
            820                 825                 830
Ile Leu Lys Trp Glu Ala Tyr Ile Phe Gln Met Gln Pro Arg Leu Gln
            835                 840                 845
Leu Ala Val Thr His Phe Pro Ser Glu Cys Thr Val Glu Arg Ile Ile
        850                 855                 860
Leu Leu Gly Leu Ser Pro Gly Ala Lys Thr Ala Leu Ile Glu Pro Gly
865                 870                 875                 880
Asn Lys Lys Val Glu Ile Glu Leu Gly Pro Leu Phe Ile Gln Gly Asn
                885                 890                 895
Arg Gly Ser Val Pro Thr Ile Arg Lys Pro Asn Val Arg Ile Thr Asp
                900                 905                 910
Asp Trp Ser Ile Gln Ile Leu
```

-continued

```
<210> SEQ ID NO 18
<211> LENGTH: 7
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 18 catatgg                                                                 7

<210> SEQ ID NO 19
<211> LENGTH: 7
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 19 cccatgg                                                                 7
```

PLANT ALPHA-GLUCOSIDASE II HOMOLOGS

This application claims the benefit of U.S. Provisional Application No. 60/107,909, filed Nov. 10, 1998.

FIELD OF THE INVENTION

This invention is in the field of plant molecular biology. More specifically, this invention pertains to nucleic acid fragments encoding alpha-glucosidase II subunits in plants and seeds.

BACKGROUND OF THE INVENTION

Catabolism is a key determinant of the actual steady-state level of a particular metabolite. For example, levels of oligosaccharides and complex carbohydrates such as starch in plants are determined by both enzymes involved in their synthesis as well as enzymes involved in their degradation. Among the enzynes involved in carbohydrate catabolism is alpha-glucosidase. An exo-carbohydrase, the enzyme hydrolyzes the terminal, non-reducing 1,4-linked D-glucose residues in malto-oligosaccharides and starch releasing D-glucose. Different isoforms of alpha-glucosidase that vary in substrate specificities and pH optima have been characterized in plants. In spinach, isoforms I and II use starch and a range of malto-oligosaccharides as substrates whereas isoforms III and IV only use malto-oligosaccharides (Sugimoto et al. (1997) *Plant Mol Biol* 33:765–768). In mammalian systems, glucosidase I and glucosidase II are known to be sequentially involved in the trimming of glucose residues from N-linked glycans on newly synthesized glycoproteins in the endoplasmic reticulum (ER) (Kalz-Fuller et al. (1995) *Eur J Biochem* 231:344–351; Trombetta et al. (1996) *J Biol Chem* 271:27509–27516). Alpha-glucosidase II is composed of two subunits, alpha and beta, with the alpha subunit harboring the catalytic activity, while the smaller subunit which contains a putative ER retention signal (HDEL) at the C terminus, may be involved in localizing the enzyme to the ER (Trombetta et al. (1996) *J Biol Chem* 271:27509–27516).

Plant glucosidase genes have been isolated from various species, including spinach (Sugimoto et al. (1997) *Plant Mol Biol* 33:765–768), potato (Taylor et al. (1998) *Plant J* 13:419–425), and barley (Tibbot and Skadsen (1996) *Plant Mol Biol* 30:229–241; U.S. Pat. No. 5,763,252). Expectedly, high gene expression is observed during germination stages, when starch reserves are broken down to supply the energy needed for growth (Tibbot and Skadsen (1996) *Plant Mol Biol* 30:229–241; Taylor et al. (1998) *Plant J* 13:419–425). There is a great deal of interest in identifying the genes that encode alpha-glucosidases in plants. These genes may be used in plants to control carbohydrate levels in plants and seeds or to manipulate glycoprotein processing. Accordingly, the availability of nucleic acid sequences encoding all or a portion of these alpha-glucosidase II enzymes would facilitate studies to better understand plant metabolism, and provide genetic and biochemical tools for the manipulation of the starch/sucrose content in plants and seeds, and mass-production of the enzyme for post-harvest starch modification.

SUMMARY OF THE INVENTION

The present invention relates to isolated polynucleotides comprising a nucleotide sequence encoding a first polypeptide of at least 50 amino acids that has at least 80% identity based on the Clustal method of alignment when compared to a polypeptide selected from the group consisting of a corn alpha-glucosidase II alpha subunit polypeptide of SEQ ID NO:2, a rice alpha-glucosidase II alpha subunit polypeptide of SEQ ID NO:4, a soybean alpha-glucosidase II alpha subunit polypeptide of SEQ ID NO:6, a soybean alpha-glucosidase II alpha subunit polypeptide of SEQ ID NO:8, and a wheat alpha-glucosidase II alpha subunit polypeptide of SEQ ID NO:10. The present invention relates to isolated polynucleotides comprising a nucleotide sequence encoding a first polypeptide of at least 50 amino acids that has at least 70% identity based on the Clustal method of alignment when compared to a polypeptide selected from the group consisting of a corn alpha-glucosidase II beta subunit polypeptide of SEQ ID NO:12, a wheat alpha-glucosidase II beta subunit polypeptide of SEQ ID NO:14, and a wheat alpha-glucosidase II beta subunit polypeptide of SEQ ID NO:16. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, 9, 11, 13, and 15 that codes for the polypeptide selected from the group consisting of SEQ ID NOs:2, 4, 6, 8, 10, 12, 14, and 16. The present invention also relates to an isolated polynucleotide comprising a nucleotide sequences of at least one of 40 (preferably at least one of 30) contiguous nucleotides derived from a nucleotide sequence selected from the group consisting of SEQ ID NOs:1, 3, 5, 7, 9, 11, 13, and 15 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to an alpha-glucosidase II alpha subunit polypeptide of at least 50 amino acids comprising at least 80% homology based on the Clustal method of alignment compared to a polypeptide selected from the group consisting of SEQ ID NOs:2, 4, 6, 8, and 10. The present invention also relates to an alpha-glucosidase II beta subunit polypeptide of at least 50 amino acids comprising at least 70% homology based on the Clustal method of alignment compared to a polypeptide selected from the group consisting of SEQ ID NOs:12, 14, and 16.

The present invention relates to a method of selecting an isolated polynucleotide that affects the level of expression of an alpha-glucosidase II alpha or beta subunit polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level of an alpha-glucosidase II alpha or beta subunit polypeptide in the host cell containing the isolated polynucleotide; and comparing the level of an alpha-glucosidase II alpha or beta subunit polypeptide in the host cell containing the isolated polynucleotide with the level of an alpha-glucosidase II alpha or beta subunit polypeptide in a host cell that does not contain the isolated polynucleotide.

The present invention relates to a method of obtaining a nucleic acid fragment encoding a substantial portion of an alpha-glucosidase II alpha or beta subunit polypeptide gene, preferably a plant alpha-glucosidase II alpha or beta subunit polypeptide gene, comprising the steps of: synthesizing an oligonucleotide primer comprising a nucleotide sequence of at least one of 40 (preferably at least one of 30) contiguous nucleotides derived from a nucleotide sequence selected from the group consisting of SEQ ID NOs:1, 3, 5, 7, 9, 11, 13, and 15 and the complement of such nucleotide sequences; and amplifying a nucleic acid fragment (preferably a cDNA inserted in a cloning vector) using the oligonucleotide primer. The amplified nucleic acid fragment preferably will encode a portion of an alpha-glucosidase II alpha or beta subunit amino acid sequence.

The present invention also relates to a method of obtaining a nucleic acid fragment encoding all or a substantial portion of the amino acid sequence encoding an alpha-glucosidase II alpha or beta subunit polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

The present invention also relates to a composition comprising the isolated polynucleotide of the present invention.

The present invention also relates to a composition containing the polypeptide of the present invention.

The present invention also relates to an isolated polynucleotide comprising the nucleotide sequence comprising at least one of 30 contiguous nucleotides of nucleic acid sequence selected from the group consisting of SEQ ID NOs:1, 3, 5, 7, 9, 11, 13 and 15 and the complement of such sequences.

The present invention also relates to an expression cassette comprising an isolated polynucleotide of the present invention operably linked to a promoter.

The present invention also relates to a method for positive selection of a transformed cell comprising:

(a) transforming a plant cell with a chimeric gene of the present invention or an expression cassette of the present invention; and (b) growing the transformed plant cell, such as a monocot or dicot including rice, corn, wheat, or soybean, under conditions allowing expression of the polynucleotide in an amount sufficient to modify starch and/or sucrose content in a plant cell to provide a positive selection means.

BRIEF DESCRIPTION OF THE DRAWING AND SEQUENCE DESCRIPTIONS

The invention can be more fully understood from the following detailed description and the accompanying drawing and Sequence Listing which form a part of this application.

FIG. 1 depicts the amino acid sequence alignment between the alpha-glucosidase II alpha subunits encoded by the nucleotide sequences derived from soybean clone srr3c.pk003.g3 (SEQ ID NO:8) and the alpha-glucosidase-encoding nucleic acid fragment from *Solanum tuberosum* (NCBI General Identification No. 2648032, SEQ ID NO:17). Amino acids which are conserved between the two sequences are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Alpha-Glucosidase II Subunits

| Protein | Clone Designation | Status[a] | SEQ ID NO: (Nucleotide) | SEQ ID NO: (Amino Acid) |
| --- | --- | --- | --- | --- |
| Alpha-Glucosidase II Alpha-Subunit (Maize) | chpc24.pk0002.f10 | EST | 1 | 2 |
| Alpha-Glucosidase II Alpha Subunit (Rice) | rls48.pk0015.d3 | EST | 3 | 4 |
| Alpha-Glucosidase II Alpha Subunit (Soybean) | srr3c.pk003.g3 | EST | 5 | 6 |
| Alpha-Glucosidase II Alpha Subunit (Soybean) | srr3c.pk003.g3 | FIS | 7 | 8 |
| Alpha-Glucosidase II Alpha Subunit (Wheat) | wre1n.pk0123.a11 | EST | 9 | 10 |
| Alpha-Glucosidase II Beta Subunit (Maize) | cr1n.pk0009.f5 | EST | 11 | 12 |
| Alpha-Glucosidase II Beta Subunit (Wheat) | wlm0.pk0008.d11 | EST | 13 | 14 |
| Alpha-Glucosidase II Beta Subunit (Wheat) | wlm0.pk0008.d11 | FIS | 15 | 16 |

[a]"EST" refers to the partial sequence of the cDNA insert in the indicated cloned which has been exemplified in the provisional application. "FIS" refers to the complete sequence of the cDNA insert in the indicated clone.

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least one of 60 contiguous nucleotides, preferably at least one of 40 contiguous nucleotides, most preferably one of at least 30 contiguous nucleotides, of the nucleic acid sequence of the SEQ ID NOs:1, 3, 5, 7, 9, 11, 13, and 15.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, and 15 and the complement of such nucleotide sequences may be used in methods of selecting an isolated polynucleotide that affects the expression of a polypeptide such as alpha-glucosidase II subunit, such as alpha-glucosidase II alpha subunit and/or alpha-glucosidase II beta subunit in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5'non-coding sequences) and following (3'non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5'non-coding sequences), within, or downstream (3'non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Underexpression" refers to the production of a gene product in transgenic organisms at levels below that of levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of niRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several alpha-glucosidase II subunits have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other alpha-glucosidase II alpha or beta subunits, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, and 15 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as alpha-glucosidase II alpha or beta subunit) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, and 15 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of malto-oligosaccharide and starch hydrolysis and glycoprotein processing in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptide with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded alpha-glucosidase II subunit. An example of a vector for high level expression of the instant polypeptides in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLE 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| chpc24 | Corn 8 day old shoot treated 24 hrs. with herbicide MK593* | chpc24.pk0002.f10 |
| cr1n | Corn root from 7 day seedlings grown in light normalized** | cr1n.pk0009.f5 |
| rls2 | Rice leaf, 15 days after germination, 2 hrs after infection of *Magaporthe grisea* strain 4360-R-67 (avr2-yamo) | rls2.pl0014.b10 |
| rls48 | Rice leaf, 15 days after germination, 48 hrs after infection of *Magaporthe grisea* strain 4360-R-67 (avr2-yamo) | rls48.pk0015.d3 |
| sls2c | Soybean infected with *Sclerotinia sclerotiorum* mycelium. | sls2c.pk003.i20 |
| srr3c | Soybean root | srr3c.pk003.g3 |
| wlm0 | Wheat seedlings 0 hr after inoculation with *Erysiphe graminis f. sp tritici* | wlm0.pk0008.d11 |
| wre1n | Wheat seedlings 0 hr after inoculation with *Erysiphe graminis f.sp tritici*** | wre1n.pk0123.a11 |

*Application of 2-[(2,4-dihydro-2,6,9-trimethyl[1]benzothiopyrano[4,3-c]pyrazol-8-yl)carbonyl]-1,3-cyclohexanedione S,S-dioxide; synthesis and methods of using this compound are described in WO 97/19087, incorporated herein by reference.
**These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

EXAMPLE 2

Identification of cDNA Clones cDNA clones encoding alpha-glucosidase II subunits were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

EXAMPLE 3

Characterization of cDNA Clones Encoding Alpha-Glucosidase II Alpha Subunit

The BLASTX search using the EST sequences from clones chpc24.pk0002.f10. rls48.pk0015.d3, srr3c.pk003.g3 and wre1n.pk0123.a11 revealed similarity of the proteins encoded by the cDNAs to alpha-glucosidase from *Solanum tuberosum* (NCBI General Identification No. 2648032). The BLAST results for each of these ESTs are shown in Table 3:

TABLE 3

BLAST Results for Clones Encoding Polypeptides Homologous to Alpha-Glucosidase II Alpha Subunit

| Clone | BLAST pLog Score 2648032 |
|---|---|
| chpc24.pk0002.f10 | 10.70 |
| rls48.pk0015.d3 | 22.00 |
| srr3c.pk003.g3 | 27.70 |
| wre1n.pk0123.a11 | 50.50 |

The next hits in the BLASTX search for most of the above clones were alpha subunits of alpha-glucosidase II from fungal and mammalian systems. BLAST scores and probabilities indicate that the instant nucleic acid fragments encode portions of an alpha-glucosidase II alpha subunit. These sequences represent the first corn, rice, soybean and wheat sequences encoding the alpha subunit of an alpha-glucosidase II.

The cDNA insert in the soybean clone srr3c.pk003.g3 was fully sequenced. Sequencing revealed that the cDNA insert represents a full-length cDNA. The BLASTX search using the complete cDNA insert sequence revealed similarity of the polypeptide encoded by the cDNA to alpha-glucosidase from *Solanum tuberosum* (NCBI General Identification No. 2648032), with a pLog score of greater than 254.

FIG. 1 depicts the amino acid sequence alignment between the alpha-glucosidase II alpha subunits encoded by the nucleotide sequences derived from soybean clone srr3c.pk003.g3 (SEQ ID NO:8) and the alpha-glucosidase-encoding nucleic acid fragment from *Solanum tuberosum* (NCBI General Identification No. 2648032, SEQ ID NO:17). The two amino acid sequences are 70.2% identical.

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode all or a substantial portion of an alpha-glucosidase II alpha subunit. These sequences represent the first monocot (corn, rice, and wheat) and soybean sequences encoding the alpha subunit of an alpha-glucosidase II.

EXAMPLE 4

Characterization of cDNA Clones Encoding Alpha-Glucosidase II Beta Subunit

The BLASTX search using the EST sequences from clones cr1n.pk0009.f5, rls2.pk0014.b10, sls2c.pk003.i20 and wlm0.pk0008.d11 revealed similarity of the proteins encoded by the cDNAs to alpha-glucosidase beta subunit from *Mus musculus* (NCBI General Identification No. 2104691). The BLAST results for each of these ESTs are shown in Table 4:

TABLE 4

BLAST Results for Clones Encoding Polypeptides Homologous to Alpha-Glucosidase II Beta Subunit

| Clone | BLAST pLog Score 2104691 |
|---|---|
| cr1n.pk0009.f5 | 7.52 |
| rls2.pk0014.b10 | 5.00 |
| sls2c.pk003.i20 | 5.40 |
| wlm0.pk0008.d11 | 11.10 |

The cDNA insert in the wheat clone wlm0.pk0008.d11 was fully sequenced. The BLASTX search using the complete sequence of the cDNA insert in clone wlm0.pk0008.d11 revealed similarity of the polypeptide encoded by the cDNA to alpha-glucosidase beta subunit from *Mus musculus* (NCBI General Identification No. 2104691) with a pLog score of 12.50. The amino acid sequence derived from the complete sequence of the cDNA insert in clone wlm0.pk0008.d11 showed 27.5% identity to the amino acid sequence of the alpha-glucosidase beta subunit from *Mus musculus* (NCBI General Identification No. 2104691), and 67.9% identity to an amino acid sequence that may be derived from a maize EST in the public database (NCBI General Identification No. 5455860) when translated. Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

BLAST scores and probabilities indicate that the nucleic acid fragments comprising % identity the instant cDNA clones encode a substantial portion of an alpha-glucosidase II beta subunit. These sequences represent the first plant sequences encoding alpha-glucosidase II beta subunit.

EXAMPLE 5

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™, Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

EXAMPLE 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1983) *Gene* 25:179–188) and the 3' region of the nopaline synthase gene from the T-DNA of the Ti plasmid of *Agrobacterium tumefaciens.* The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

EXAMPLE 8

Assaying Alpha-Glucosidase II Activity

The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays to verify over- or underexpression of functional alpha-glucosidase II protein in transgenic plants and transformed bacterial cells. Assays may be conducted under well known experimental conditions which permit optimal enzymatic activity. For example, assays for alpha-glucosidase II are presented by Trombetta et al. (1996) *J Biol Chem* 271:27509–27516 and Taylor et al. (1998) *Plant J* 13:419–425.

What is claimed is:

1. An isolated polynucleotide comprising:
   (a) a nucleotide sequence encoding a polypeptide having plant alpha glucosidase II alpha subunit activity, wherein the amino acid sequence of the polypeptide and the amino acid sequence of SEQ ID NO:8 have at least 80% identity based on the Clustal alignment method, or
   (b) the complement of the nucleotide sequence.

2. The polynucleotide of claim 1, wherein the amino acid sequence of the polypeptide and the amino acid sequence of SEQ ID NO:8 have at least 85% identity based on the Clustal alignment method.

3. The polynucleotide of claim 1, wherein the amino acid sequence of the polypeptide and the amino acid sequence of SEQ ID NO:8 have at least 90% identity based on the Clustal alignment method.

4. The polynucleotide of claim 1, wherein the amino acid sequence of the polypeptide and the amino acid sequence of SEQ ID NO:8 have at least 95% identity based on the Clustal alignment method.

5. The polynucleotide of claim 1 comprising the nucleotide sequence of SEQ ID NO:7.

6. The polynucleotide of claim 1, wherein the polypeptide comprises the amino acid sequence of SEQ ID NO:8.

7. A chimeric gene comprising the polynucleotide of claim 1 operably linked to a regulatory sequence.

8. A vector comprising the polynucleotide of claim 1.

9. A method for transforming a cell comprising transforming a cell with the polynucleotide of claim 1.

10. A cell comprising the chimeric gene of claim 7.

11. A method for transforming a plant comprising transforming a plant cell with the polynucleotide of claim 1 and regenerating a plant from the transformed plant cell.

12. A plant comprising the chirneric gene of claim 7.

13. A seed comprising the chimeric gene of claim 7.

* * * * *

UNITED STATES PATENT AND TRADEMARK OFFICE
CERTIFICATE OF CORRECTION

PATENT NO.     : 6,316,698 B1                                       Page 1 of 1
DATED          : November 13, 2001
INVENTOR(S)    : Allen Stephen M. and Kinney Anthony J.

It is certified that error appears in the above-identified patent and that said Letters Patent is hereby corrected as shown below:

<u>Column 52,</u>
Line 43, delete "chirneric" and insert -- chimeric --.

Signed and Sealed this

Fifteenth Day of June, 2004

JON W. DUDAS
*Acting Director of the United States Patent and Trademark Office*